(12) United States Patent
Khalaj et al.

(10) Patent No.: US 11,364,050 B2
(45) Date of Patent: Jun. 21, 2022

(54) CATHETER PLACING INSTRUMENT

(71) Applicant: Avent, Inc., Alpharetta, GA (US)

(72) Inventors: Steve S. Khalaj, Laguna Hills, CA (US); Eric A. Schepis, Alpharetta, GA (US); Thomas D. Mina, Newport Beach, CA (US)

(73) Assignee: Avent, Inc., Alpharetta, GA (US)

( * ) Notice: Subject to any disclaimer, the term of this patent is extended or adjusted under 35 U.S.C. 154(b) by 265 days.

(21) Appl. No.: 16/286,769

(22) Filed: Feb. 27, 2019

(65) Prior Publication Data

US 2020/0268413 A1 Aug. 27, 2020

(51) Int. Cl.
| | | |
|---|---|---|
| *A61B 17/34* | (2006.01) | |
| *A61N 1/05* | (2006.01) | |
| *A61M 25/02* | (2006.01) | |
| *A61M 25/01* | (2006.01) | |

(Continued)

(52) U.S. Cl.
CPC ...... *A61B 17/3468* (2013.01); *A61B 17/3415* (2013.01); *A61M 25/01* (2013.01); *A61M 25/02* (2013.01); *A61N 1/0504* (2013.01); *A61M 25/0041* (2013.01); *A61M 25/09041* (2013.01); *A61M 2025/024* (2013.01); *A61M 2025/028* (2013.01)

(58) Field of Classification Search
CPC ............ A61B 17/3403; A61B 17/3415; A61B 17/3468; A61B 1/00149; A61B 2017/3405; A61B 2017/3407; A61B 2017/3409; A61B 2017/00469; A61B 2017/347; A61B 2017/00424; A61B 2017/0042; A61M 2025/09116; A61M 25/01; A61M 25/0105; A61M 25/0113; A61M 25/0133; A61M 25/09; A61M 25/09041; A61M 25/0041; A61M 25/02; A61M 2025/024; A61M 2025/028; A61N 1/0504

See application file for complete search history.

(56) References Cited

U.S. PATENT DOCUMENTS 4,858,810 A * 8/1989 Intlekofer ............... A61B 17/22
226/127
5,007,914 A * 4/1991 Schweigerling ..... A61B 17/282
606/108

(Continued)

OTHER PUBLICATIONS

International Search Report and Written Opinion for PCT/US2020/017593, dated Jun. 19, 2020, 15 pages.

*Primary Examiner* — Tan-Uyen T Ho
*Assistant Examiner* — Rachel S Highland
(74) *Attorney, Agent, or Firm* — Dority & Manning, P.A.

(57) ABSTRACT

A catheter placing instrument is provided. The catheter placing instrument includes an elongated body that extends in a longitudinal direction from a proximal end to a distal end. The elongated body has a top surface configured to receive a catheter extending from the proximal end to the distal end. The elongated body includes a catheter insertion section and a grip section. The catheter insertion section includes a catheter locking clamp located at the distal end of the elongated body, and the grip section includes a catheter guide. The catheter placing instrument can be used to place or implant any tubular medical device within a patient's body. A method of placing a tubular medical device at a deep location within a patient's body is also provided.

20 Claims, 3 Drawing Sheets

(51) Int. Cl.
    *A61M 25/00*    (2006.01)
    *A61M 25/09*    (2006.01)

(56) References Cited

U.S. PATENT DOCUMENTS

| | | | | |
|---|---|---|---|---|
| 5,176,647 | A * | 1/1993 | Knoepfler | A61B 17/3415 |
| | | | | 604/158 |
| 5,325,746 | A * | 7/1994 | Anderson | A61B 17/22 |
| | | | | 24/115 M |
| 6,059,484 | A * | 5/2000 | Greive | A61M 25/09041 |
| | | | | 128/912 |
| 7,717,865 | B2 * | 5/2010 | Boutillette | A61M 25/09041 |
| | | | | 600/585 |
| 8,202,254 | B2 * | 6/2012 | Schweikert | A61M 25/09041 |
| | | | | 604/171 |
| 8,298,181 | B2 * | 10/2012 | Perez | A61M 5/3287 |
| | | | | 604/115 |
| 9,320,872 | B2 * | 4/2016 | Urmey | A61N 1/36017 |
| 2005/0096566 | A1 * | 5/2005 | Arnott | A61M 25/09041 |
| | | | | 600/585 |
| 2010/0204646 | A1 | 8/2010 | Plicchi et al. | |
| 2012/0010627 | A1 * | 1/2012 | Watschke | A61M 25/01 |
| | | | | 606/129 |
| 2015/0133951 | A1 | 5/2015 | Seifert et al. | |
| 2017/0100161 | A1 * | 4/2017 | Asleson | A61B 17/3468 |
| 2017/0303940 | A1 * | 10/2017 | Sperry | A61B 17/3417 |
| 2018/0117288 | A1 * | 5/2018 | Lindsay | A61M 27/002 |
| 2018/0296799 | A1 * | 10/2018 | Horst | A61M 25/0618 |

* cited by examiner

CATHETER PLACING INSTRUMENT

FIELD OF THE INVENTION

The subject matter of the present invention relates generally to an instrument for placing a catheter in deep anatomical areas of the human body where visualization may be difficult.

BACKGROUND

Catheters are used in many clinical settings as devices for delivering fluid, treating an obstructed body cavity, draining fluid, and otherwise providing accesses to deep locations within the human body. While catheters of various types are highly useful, proper placement of a catheter is often a difficult procedure which can often require the insertion of a catheter, e.g., by blunt dissection during open surgery, to a blind location not visible to a surgeon, doctor, or other clinical professional. Blunt dissection involves the careful separation of tissues along tissue planes by either fingers or blunt instrument(s), without slicing through tissues using sharp or heat-actuated devices.

For example, fluid delivery catheters are often used as part of a catheter-based infusion system to both block the nerve bundles for a surgery or after a trauma, and to provide a continuous, low flow rate of the anesthetic over a period of time (e.g., 2-5 days following surgery) for post-operative pain management. In one example procedure, total knee arthroplasty, a fluid delivery catheter is inserted from an open surgical wound site blindly into the adductor canal at a distance of about 10-20 cm using a generic elongated surgical tool. Most often, this procedure is performed using a pituitary ronguer by holding a distal tip of the catheter in the alligator jaws at the distal end of the tool and bluntly dissecting the deep tissue to access the delivery site of the catheter. However, pituitary ronguers are designed for use to remove spinal bone or disc tissue and are not optimized for catheter placement.

Furthermore, existing surgical tools for catheter placement at deep locations do not provide any indication of the depth of insertion of the catheter, thus requiring surgeons to blindly approximate or estimate the depth at which a catheter has been placed.

Consequently, there is a need for a catheter placing instrument that is optimized for blind insertion into deep anatomical areas. In particular, a catheter placing instrument that provides an indication of the depth of the catheter placement at a deep anatomical area would also be useful.

SUMMARY

The present invention provides a catheter placing instrument. The catheter placing instrument includes an elongated body, the elongated body extending in a longitudinal direction from a proximal end to a distal end, the elongated body having a top surface configured to receive a catheter extending from the proximal end to the distal end. The elongated body includes a catheter insertion section and a grip section. The catheter insertion section includes a catheter locking clamp located at the distal end of the elongated body. The grip section includes a catheter guide.

In one particular embodiment, the grip section can further include a locking mechanism, wherein the locking mechanism is configured to lock and unlock the catheter locking clamp. Further, the locking mechanism can include an actuator positioned on the grip section.

In another embodiment, the catheter placing instrument can further include measurement markings extending from the distal end of the elongated body along at least one side wall of the catheter insertion section such that, when a catheter is positioned on the top surface, the measurement markings are viewable on the side wall.

In an additional embodiment, the catheter guide can include at least two protrusions extending vertically above the top surface.

In one more embodiment, the catheter locking clamp can include at least two clamp arms configured to lock a catheter in place against the top surface of the elongated body.

In yet another embodiment, the catheter insertion section has a height $H_1$ in a vertical direction that is shorter than a height $H_2$ of the grip section in the vertical direction.

In still another embodiment, the catheter insertion section has a width $W_1$ in a transverse direction, and the grip section has a width $W_2$ in the transverse direction. Further, the width $W_2$ of the grip section can be larger than the width $W_1$ of the catheter insertion section.

In an additional embodiment, the grip section can include a grip handle.

In a further embodiment, the top surface can be flat.

In one more embodiment, the top surface can include a concave curvature configured to hold a catheter.

In a further embodiment, the catheter placing instrument can be configured to place a catheter at a deep anatomical site of a patient.

In yet another embodiment, the catheter placing instrument can be configured to place an electrical lead having one or more electrical contacts at a deep anatomical site of a patient.

The present invention also provides a method of surgically placing a tubular medical device at a deep anatomical site of a patient. The method includes steps of: inserting a tubular medical device into an open surgical site; providing a placing instrument. The placing instrument includes: an elongated body, the elongated body extending in a longitudinal direction from a proximal end to a distal end, the elongated body having a top surface configured to receive a tubular medical device extending from the proximal end to the distal end, wherein the elongated body comprises a device insertion section and a grip section; wherein the tubular medical device insertion section comprises a locking clamp located at the distal end of the elongated body; and wherein the grip section comprises a tubular medical device guide. The method includes additional steps of: placing the tubular medical device on the top surface of the placing instrument such that a distal tip of the tubular medical device is positioned at the distal end of the elongated body and the tubular medical device extends through the tubular medical device guide; locking the tubular medical device to the placing instrument by clamping the distal tip of the tubular medical device with the locking clamp; advancing the distal end of the placing instrument into a deep anatomical location accessed by the open surgical site; releasing the release mechanism to unlock the tubular medical device from the placing instrument; and removing the placing instrument from the deep anatomical location without moving the tubular medical device.

In one particular embodiment of the method, the tubular medical device can be a catheter.

In another embodiment, the tubular medical device can be an electrical lead having at least one electrical contact.

In an additional embodiment, the placing instrument can further include measurement markings extending from the distal end of the elongated body along the longitudinal length of the tubular medical device insertion section; wherein the step of advancing includes advancing the distal end of the tubular medical device to the anatomical location to a desired depth utilizing the measurement markings to determine the depth.

In yet another embodiment, the step of advancing can include blindly advancing the distal end of the placing instrument into a deep anatomical location by blunt dissection.

In still another embodiment, the tubular medical device includes a viewable indicator. Moreover, the step of removing the placing instrument from the anatomical location without moving the tubular medical device can include visualizing the viewable indicator to ensure that the tubular medical device is not moved when the placing instrument is removed from the anatomical location.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment.

To assist in the description of the system and method of use disclosed herein, the following terms are used. The "wound site" is the area within the body of the patient where the surgical procedure was performed. The "incision site" is the area where the surgeon entered through the patient's skin to arrive at the wound site. The incision site need not be made by the surgeon, for example, a patient may have an open wound through which the surgeon arrives at the wound site. The "pierce site" is the site where the patient's skin is pierced to allow the catheter to extend therethrough and arrive at the wound site. The term "distal" refers to a site that is away from a specified site. The term "proximal" refers to a site that is close to a specified site. Expressed alternatively, a site termed "proximal" is measurably closer to a specified reference point than a site termed "distal."

Generally speaking, the present invention is directed to a catheter placing instrument having an elongated body that extends in a longitudinal direction from a proximal end to a distal end. The elongated body has a top surface configured to receive a catheter extending from the proximal end to the distal end. The elongated body includes a catheter insertion section and a grip section. The catheter insertion section includes a catheter locking clamp located at the distal end of the elongated body, and the grip section includes a catheter guide. The catheter placing instrument can be used to place a catheter, an electrical lead, or any other tubular medical device at a deep anatomical location of a patient. Specific features of the catheter placing instrument of the present invention may be better understood with reference to FIGS. 1-5.

Figure 1:
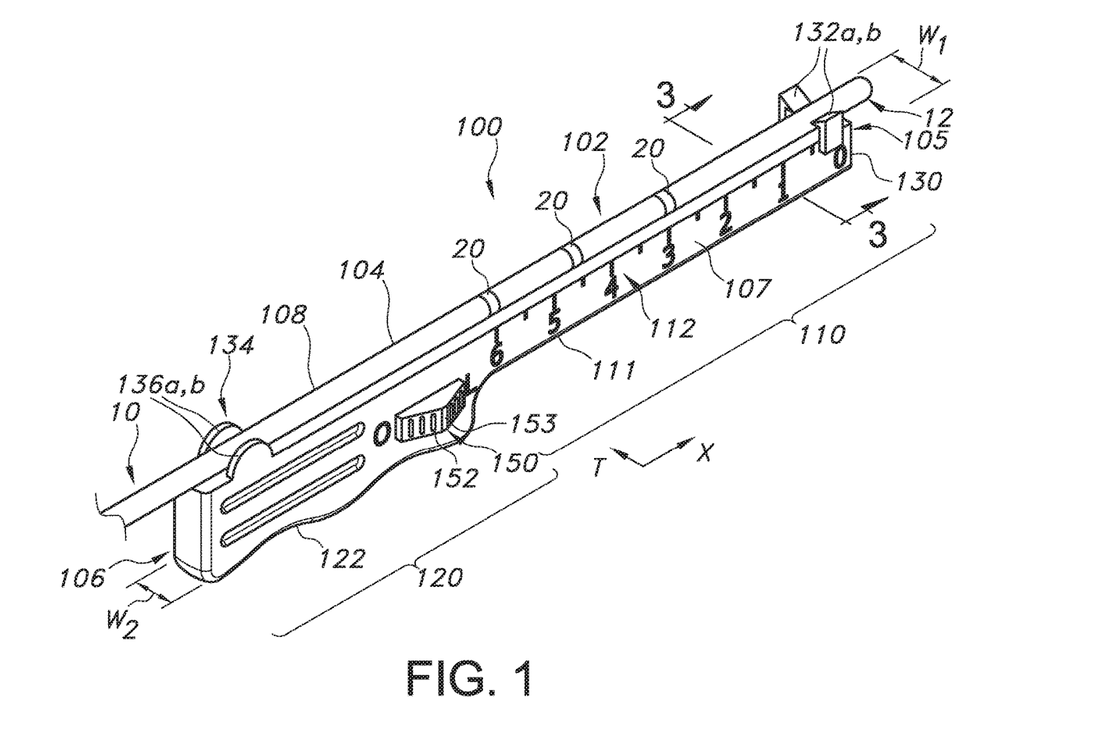
FIG. 1 is a perspective view of a catheter placing instrument according to one particular embodiment of the present invention.

Referring now to FIG. 1, one embodiment of the catheter placing instrument 100 of the present invention is shown. Although a catheter 10 is shown for demonstration in FIG. 1, it should be understood that the catheter placing instrument 100 can be used to place or implant a catheter 10 or any other tubular medical device, such as an electrical lead having at least one electrical contact or other tubular medical device. The catheter placing instrument 100 comprises an elongated body 102 extending from a proximal end 106 to a distal end 105 along a longitudinal axis X. The elongated body 102 has a top surface 104 extending from the proximal end 106 to the distal end 105. The top surface 104 is configured to receive a catheter 10, as shown in FIG. 1. The elongated body 102 is formed by a catheter insertion section 110 configured to extend deep into the patient's tissue to place the catheter 10, and a grip section 120 configured to be held by a surgeon to guide the placement of the catheter 10. The catheter insertion section 110 of the catheter placing instrument 100 extends from the distal end 105 of the elongated body 102 to the grip section 120 along the longitudinal axis X. The grip section 120 extends from the proximal end 106 of the elongated body 102 to the catheter insertion section 110.

Figure 2:
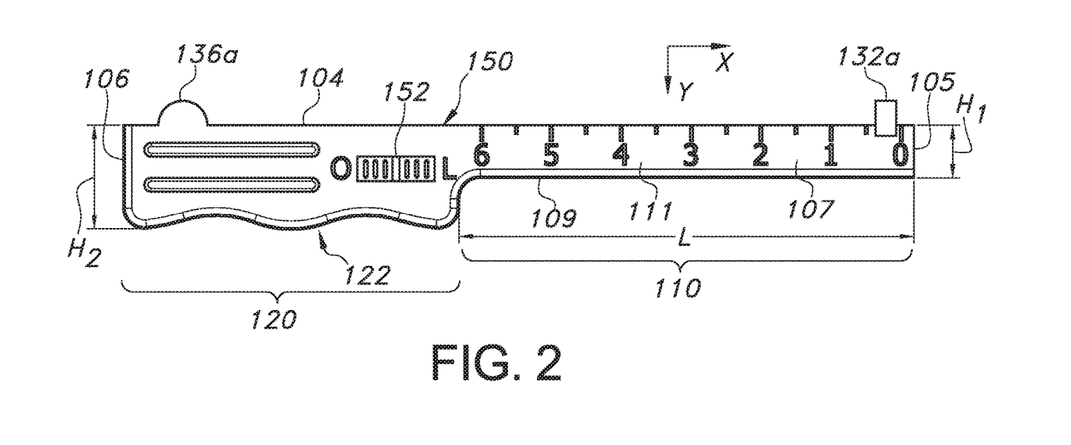
FIG. 2 is a side view of the catheter placing instrument of FIG. 1.
Figure 3A:
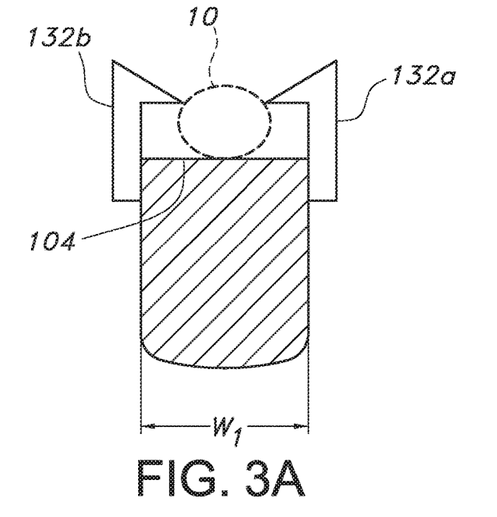
FIGS. 3A-B illustrate cross-sectional views along line 3-3 of two embodiments of the top surface of the catheter placing instrument of FIG. 1.
Figure 3B:
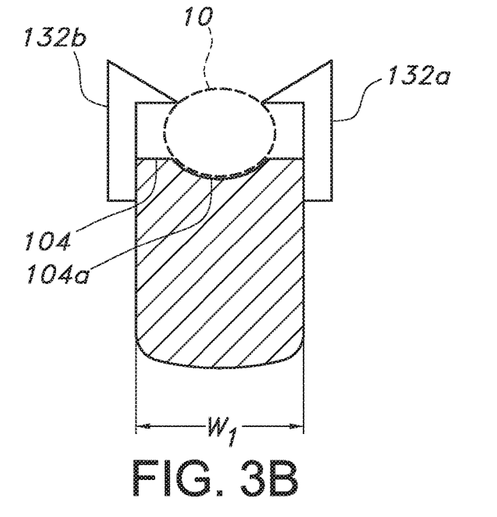

As best illustrated in FIGS. 1, 2 and 3A-B, the top surface 104 of the elongated body 102 extends continuously from the distal end 105, through the catheter insertion section 110 and the grip section 120 to the proximal end 106 of the elongated body 102. The top surface 104 can be flat, as shown in FIG. 3A, or it can have a concave curvature forming a channel 104a extending from the distal end to the proximal end 106, as shown in FIG. 3B. The channel 104a can be configured to hold or cradle the catheter 10 in place. The channel 104a can extend across the entire width of top surface 104 or can extend across just a portion of the width of the top surface 104, as shown in FIG. 3B.

As shown in FIG. 1, the catheter insertion section 110 can be in the form of a shaft 111, as shown in FIGS. 1 and 2. The shaft 111 can be defined by the top surface 104, a first side 107, a second side 108, and a bottom surface 109 of the elongated body 102. The catheter insertion section 110, e.g., shaft 111, is formed such that it is stiff enough to be capable of being pushed through the tissue, muscle or other structure to form a path through the body by blunt dissection. The catheter insertion section 110 can be made of a polymer, metal, or other material or combination of materials, e.g., polymer and metal.

As shown in FIGS. 1-2, the shaft 111 can have a length L in the longitudinal direction, a width $W_1$ across the top surface 104 of the elongated body 102 in a transverse direction T, and a height $H_1$ extending down in a vertical direction V perpendicular to both the top surface 104 and the longitudinal axis X. The width $W_1$ can be constant along the length L of the shaft 111, or alternatively, the width $W_1$ can vary along the length L of the shaft. For example, in one alternative embodiment, the width $W_1$ and/or the height $H_1$ can increase toward the distal end compared to the proximal end of the shaft 111. The increase in width and/or height of the shaft 111 can enable improved tunneling performance by increasing rigidness or stiffness at the distal end. In another embodiment, the width $W_1$ and/or the height $H_1$ can decrease toward the distal end compared to the proximal end of the shaft 111. The decrease in width and/or height of the shaft 111 can aid in reducing interference with the patient's tissue by reducing the cross-sectional area of the distal end of the shaft 111. In yet another embodiment, the distal end of the shaft 111 and the proximal end of the shaft 111 adjacent to the grip section 120 may have a greater width and/or height compared to a middle portion of the shaft 111.

The length L of the shaft 111 is configured to be at least as long as a perfusion segment of a catheter. For example, the shaft 111 can have a length L in a range from about 1 inch to about 20 inches, such as from about 2 inches to about 15 inches, or from about 4 inches to about 10 inches.

The grip section 120 can form a handle 122, illustrated in FIGS. 1-2, for a user to grip and hold the catheter placing instrument 100. The grip section 120 can be defined by the top surface 104, first side 107, second side 108, and bottom surface 109. In one possible embodiment, as illustrated in FIG. 1, the first and second sides of the grip section 120 can be continuous and/or coplanar with the first side 107 and second side 108 of the shaft 111.

As shown in FIGS. 1-2, the grip section 120 has a height $H_2$ extending down in a vertical direction from the top surface 104 that is equal to or greater than the height $H_1$ of the shaft 111. The height $H_2$ can be constant through the entire grip section 120 or can be varied. For example, as shown in FIGS. 1-2, the bottom surface of the grip section 120 is concavely curved in several locations to form a better surface for gripping with a user's fingers, resulting in a varying height $H_2$ along the longitudinal axis x. Additionally, the grip section 120 has a width $W_2$ at the proximal end of the elongated body 102 that is equal to or greater than the width $W_1$ of the shaft 111.

The grip section 120 of the catheter placing instrument 100 may also be made of a polymer, metal, or other material or combination of materials, e.g., a polymer and a metal. The grip section 120 and the catheter insertion section 110 may, in some instances, be constructed of the same material or combination of materials. For example, the elongate body 102 can be formed of a single, unitary piece of material, such as a rigid polymer or metal. In other instances, the grip section 120 and the catheter insertion section 110 can be formed of separate components that are attached together to form the elongate body 102, e.g., via a two-piece construction. For example, grip section 120 may be made of polymer and catheter insertion section 110 may be made of metal and attached to the grip section 120 to form the elongate body 102, or alternatively, the grip section 120 can be made of metal and the catheter insertion section 110 can be made of polymer. Example metals or alloys from which grip section 120 or catheter insertion section 110 may be constructed include, but are not limited to, stainless steel, titanium, titanium alloys, nickel-cobalt, and nickel-cobalt alloys. Example polymers may include, but are not limited to, acetal resin, polyether ether ketone (PEEK), polycarbonate, polypropylene composites, and liquid-crystal polymer (LCP). In some instances, elongated body 102 may be a single, unitary piece of material. In other embodiments, grip section 102 may be removable (not shown).

Further, the distal end 105 of the shaft 111 of the elongated body 102 may be shaped to aid in tunneling through tissue or muscle. For example, the distal end 105 may be tapered, angled, blunt, rounded, pointed, bent, or otherwise shaped to enable a user to perform blunt dissection through subcutaneous tissue without excess damage to surrounding tissue, piercing through the skin, or coring of the tissue.

Still referring to FIG. 1, at the distal end 105 of the catheter insertion section 110, e.g., shaft 111, there is a catheter locking clamp 130. The catheter locking clamp 130 is configured to lock a catheter 10 in place with respect to the distal end of the elongated body 102. In one possible embodiment, the catheter locking clamp 130 includes at least two clamping arms 132a and 132b to clamp and hold the catheter 10 in place. The arms 132a and 132b of the catheter locking clamp 130 can be positioned on the top surface 104 or can be connected to the first side 107 and second side 108 of the shaft 111 at the distal end 105 of elongated body 102.

The locking and unlocking of the catheter locking clamp 130 can be controlled by a locking mechanism 150. The locking mechanism 150 can have an actuator 152 to initiate the locking or unlocking of the clamp 130. The actuator 152 can preferably be located on the grip section 120 of the catheter placing instrument 100 for convenient access by a user holding the grip section 120. The actuator 152 can be in the form of any suitable mechanism for initiating the unlocking (opening) and locking (closing) of the catheter locking clamp 130. For example, as illustrated in FIG. 1, the actuator 152 can be in the form of a sliding lock/unlock button. A sliding lock/unlock button as shown in FIG. 1 can slide one direction along the longitudinal axis of the elongated body 102 to lock the clamp 130 and can slide in an opposite direction along the longitudinal axis to unlock the clamp 130 and release the catheter 10. In a similar embodiment, a sliding lock/unlock button actuator 152 could slide along an axis perpendicular to the longitudinal axis of the elongated body 102 to lock or unlock the clamp 130 or be oriented along any other axis. The actuator 152 of FIG. 1 can have a shape that is sloped or curved toward an apex 153 in order to create an ergonomic shape for a user's finger to grip the sliding button 152 to slide it back and forth.

As shown in FIG. 1, at the proximal end 106 of the elongated body 102, there is additionally a catheter guide 134. The catheter guide 134 is configured to guide the placement of the catheter 10 on the top surface 104 at the opposite end from the catheter locking clamp 130. The catheter guide 134 can include protrusions 136a and 136b positioned on the top surface 104 or on the first side 107 and second side 108 of the grip section 120 at the proximal end 106 of the elongated body 102. The protrusions 136a and 136b can extend vertically above the top surface 104. The protrusions 136a and 136b are configured to guide the catheter 10 to rest between the protrusions 136a and 136b on the top surface 104 of the elongated body 102. The protrusions 136a and 136b can be integrally formed with the elongate body 102 or can be adhered or otherwise attached to the elongate body 102 by any suitable permanent or removable attachment means. The catheter guide 134 can form a cross-sectional shape with the top surface 104 that is generally C-shaped, generally U-shaped, generally horseshoe-shaped, or any other suitable shape to form vertical guides on either side of the top surface 104 to guide the placement of the catheter 10 on the top surface 104.

As shown in FIGS. 1-2, the elongated body 102 includes measurement markings 112 on at least one of the first side 107 and the second side 108 of the catheter insertion section 110, e.g., on the first side 107 and the second side 108 of the shaft 111. The measurement markings 112 can begin at the location of the catheter locking clamp 130 and can extend along a length of the catheter insertion section 110 towards the proximal end 106 of the elongated body 102. The measurement markings 112 can extend for a portion of the length L of the catheter insertion section 110 or can extend the entire length L of the catheter insertion section 110 to the grip section 120. For example, there can be a measurement marking "zero" at the position of the catheter locking clamp 130 and the measurement markings 112 can increase in a proximal direction towards the grip section 120 in order to notify a user of the depth of insertion of the catheter insertion section 110. Alternatively, or in addition, there can be measurement markings 112 which begin at zero at the proximal end 106 of the catheter insertion section 110 and increase toward the distal end 105 of the catheter insertion section 110. The measurement markings 112 can measure distance in inches, cm, or both, or any other imperial or metric units of length, and can provide markings at any suitable intervals, such as whole integers or fractions of a unit. In one embodiment, there can be a vertical linear marking every 1/16 of an inch, with every 1/2 inch marked with a longer and/or wider vertical marking, and a numerical indicator of the insertion depth at each full integer unit as shown in FIG. 1. The markings 112 may be laser etched, printed, integrally formed (such as molded) with the elongated body 102 or shaft 111, or otherwise placed on the elongated body 102.

Figure 4:
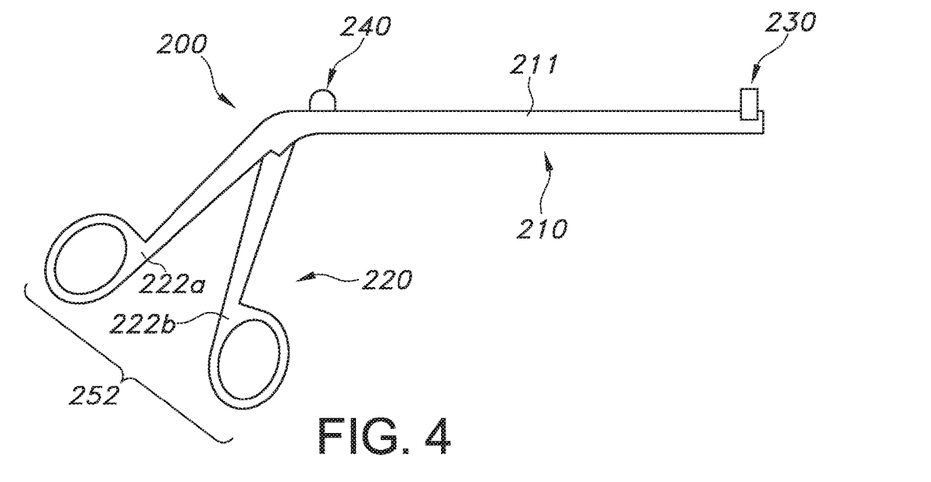
FIG. 4 illustrates a side view of an alternative embodiment of a catheter placing instrument.
Figure 5:
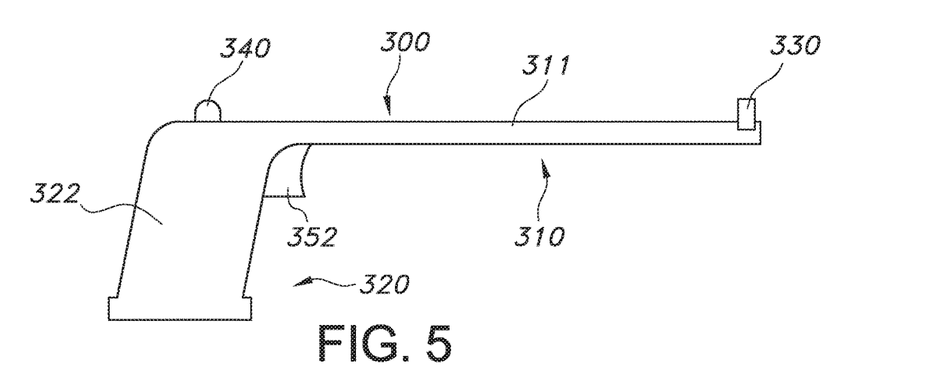
FIG. 5 illustrates a side view of yet another possible embodiment of a catheter placing instrument.

FIGS. 4 and 5 illustrate alternative embodiments of the grip section and the locking mechanism actuator of the catheter placing instrument. For example, FIG. 4 illustrates a catheter placing instrument 200 having an elongated shaft 211 as the catheter insertion section 210 but has a two-handle grip section 220 including first and second handles 222a and 222b, where each handle 222a and 222b includes at least one circular opening for inserting a user's finger(s). The handles 222a and 222b form an actuator 252 for the locking mechanism 250 for the catheter locking clamp 230. Handles 222a and 222b can be squeezed closer together to actuate the catheter locking clamp 230. For example, squeezing together the handles 222a and 222b can open and unlock the catheter locking clamp 230 and returning handles 222a and 222b to their resting positions can close and lock the catheter locking clamp 230. The catheter placing instrument 200 additionally can include a catheter guide 240 having the same or similar features as the catheter guide 134 of the catheter placing instrument 100 illustrated in FIG. 1. The catheter placing instrument 200 can additionally include measurement markings 112 as described above with regard to catheter placing instrument 100.

Similarly, FIG. 5 illustrates yet another embodiment of a catheter placing instrument 300 having a trigger actuator 352 on the handle 322 forming the grip section 320 and a shaft 311 forming the catheter insertion section 310. Similarly to the embodiment of FIG. 4, catheter locking clamp 330 can be in a closed state until the trigger 352 is actuated to release and unlock the catheter locking clamp 330. The catheter placing instrument 300 additionally can include a catheter guide 340 having the same or similar features as the catheter guide 134 of the catheter placing instrument 100 illustrated in FIG. 1. The catheter placing instrument 300 can additionally include measurement markings 112 as described above with regard to catheter placing instrument 100.

Other possible embodiments of the actuator for the release mechanism include a retractable push-button actuator, either positioned on one of the sides of the grip section 120 or on a proximal end of the catheter placing instrument 100 similar to a retractable pen, or any other quick-release mechanism.

In one possible embodiment, illustrated in FIG. 1, a catheter 10 intended for use with the catheter placing instrument 100 of the present invention can include a viewable indicator, such as at least one marking 20 as an indicator of the depth of insertion or placement of the distal tip 12. For example, at least one marking 20 on the catheter 10 can be designed to align with a measurement marking 112 on the catheter placing instrument 100 to ensure that the depth of insertion of the shaft 111 actually matches the depth of insertion of the catheter 10. Thus, if the catheter 10 is removed slightly, inserted too far, or otherwise dislodged or moved from the instrument 100 during insertion, or when the instrument 100 is being removed, a user will be able to visualize that the marking(s) 20 of catheter 10 are not properly aligned and can then reposition the catheter 10. In one embodiment, the marking(s) 20 on catheter 10 can be measurement markings corresponding to those of the catheter placing instrument 100 to easily align the catheter 10 with the instrument 100.

Figure 6:
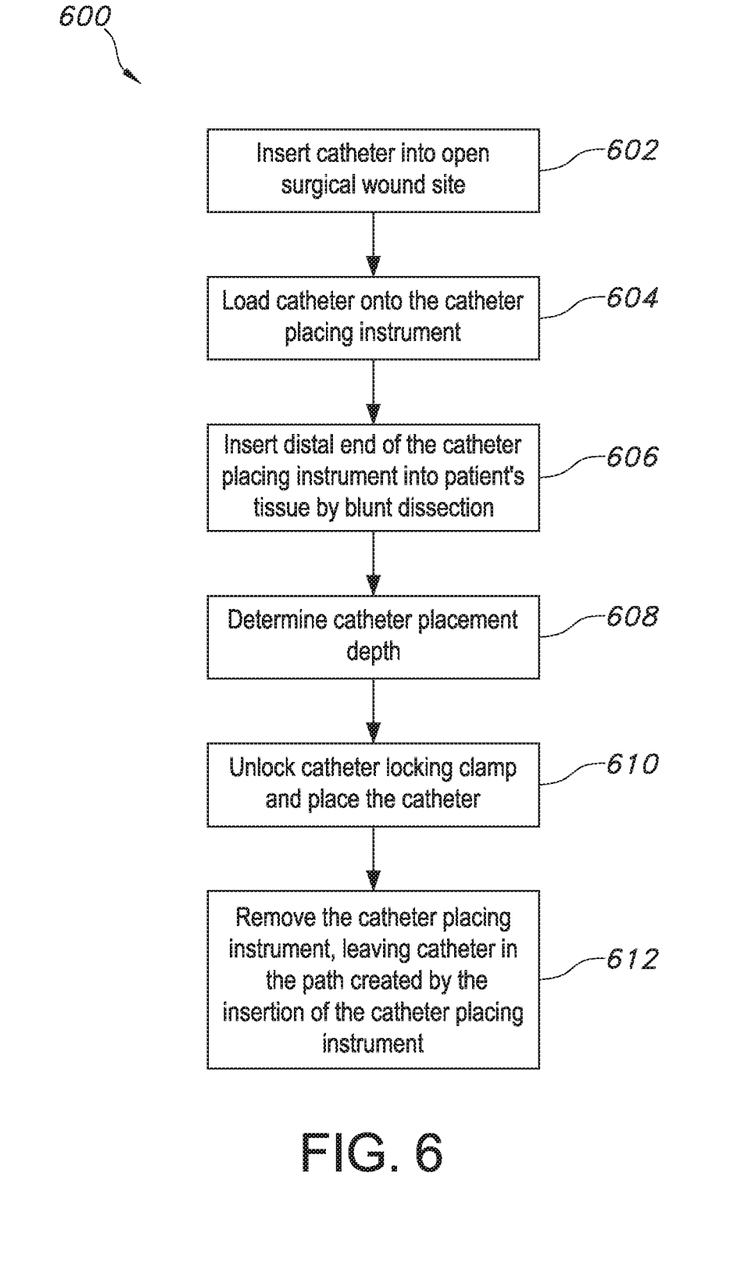
FIG. 6 illustrates a method of placing a catheter using the catheter placing instrument of the present invention.

FIG. 6 shows one exemplary surgical method 600 of using the catheter placing instrument 100 of the present invention is to place a catheter 10 to perform a nerve block for post-operative pain management during a total knee arthroplasty procedure. However, the placing instrument 100 can be used with the method steps of surgical method 600 to place or implant any other tubular medical device, such as an electrical lead having at least one electrical contact.

In a total knee arthroplasty procedure, the catheter 10 can be inserted intraoperatively into the medial intermuscular septum to provide a continuous adductor canal and periarticular nerve block. The catheter insertion can occur during a medial parapatellar, midvastus, or subvastus approach to the TKA. The medial parapatellar procedure can be performed by incising the vastus medialis oblique muscle beginning medially just above the patella and extending down to the tibial tubercle, leaving a cuff of capsular tissue on the patella for repair at closure. For the mid-vastus approach, the vastus medialis oblique muscle is split in-line with the muscle fibers at the superior pole of the patella and then incised distally to the tibial tubercle. The subvastus approach to TKA begins with an incision below the vastus medialis oblique muscle and extends to the tibial tubercle.

After the surgical approach to the knee, described above, the adductor tubercle of the epicondyle of the femur is identified. Then, the vastus medialis oblique muscle is elevated with blunt retractors to expose its deep surface and the anterior surface of the medial intermuscular septum. The medial intermuscular septum can then serve as the floor for the placement of the catheter 10. The adductor magnus tendon can be palpated beneath the medial intermuscular septum just cephalad (in the direction of the patient's head)

to the adductor tubercle. The vastus medialis oblique muscle and the adductor magnus muscle form the borders of the adductor canal. As defined above, the open surgical site is considered to be the wound site for placement of the catheter 10.

In step 602, the catheter 10 can be inserted into the open surgical wound site by any conventional procedure. For example, an introducer needle can be positioned within a T-peel sheath and inserted through a piercing site near the open surgical wound site and advanced into the wound site, the introducer needle removed, and the catheter 10 then advanced through the T-peel sheath into the open wound site. The catheter 10 can be retrieved from the T-peel sheath by grasping the distal end 12 of the catheter 10 to advance the catheter 10 through the sheath.

After advancing a length of the catheter 10 through the T-peel sheath to at least expose a length of the catheter 10 within the wound site as long as the length of the elongated body 102 of the catheter placing instrument 100, the catheter 10 can be loaded onto the catheter placing instrument 100 in step 604. First, a user ensures that the actuator 152 is released so that the catheter locking clamp 130 is unlocked. Then, the distal tip 12 of the catheter 10 is positioned in the catheter locking clamp 130 on the top surface 104 of the catheter placing instrument 100, and the catheter 10 is positioned so that it rests on the top surface 104 of the instrument 100 from the distal end 105 to the proximal end 106 and extends through the catheter guide 134 at the proximal end of the top surface 104. Then, a user can lock the catheter locking clamp 130 around the distal tip 12 of the catheter 10 to lock the catheter 10 in place. The step of locking the catheter locking clamp 130 can be performed by actuating the actuator 152, e.g., by sliding the actuator 152 of FIG. 1 in the locking direction. Now, the catheter 10 and catheter placing instrument 100 are ready for placement within the patient's tissue.

Next, in step 606, the user grasps the handle 122 of grip section 120 of the catheter placing instrument 100 and inserts the distal end 105 of the instrument 100 into the wound site and then advances the distal end 105 of the instrument cephalad along the anterior surface of the medial intermuscular septum and deep to the vastus medialis oblique muscle, e.g., about 15-20 cm cephalad to the superior patella, within the adductor canal. In step 608, the user visualizes the depth of insertion of the distal end 105 of the instrument 100 and the distal tip 12 of the catheter 10 by the measurement markings 112 on the side of the shaft 111, as shown in FIG. 1, since there is no direct visualization of the adductor canal. When the desired insertion depth has been reached, the user may place the catheter 10 or other implantable structure by releasing the actuator 152 of the catheter locking clamp 130 in step 610 and then removing the elongated body 102 while leaving the catheter 10 in the path created by the elongated body 102. Then, in step 612, the user removes the catheter placing instrument 100 by pulling the instrument 100 out of the patient's tissue in reverse of the direction of insertion.

It is to be understood that the above method is non-limiting and that the catheter placing instrument of the present invention can be used in methods of catheter insertion during other surgical procedures. Additionally, the catheter placing instrument of the present invention can be used for the implantation, insertion and/or placement of any other elongated member or device into the human body.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A catheter placing instrument comprising:
an elongated body, the elongated body extending in a longitudinal direction from a proximal end to a distal end, the elongated body having a top surface configured to receive a catheter extending from the proximal end to the distal end, wherein the elongated body comprises a catheter insertion section and a grip section, further wherein the catheter insertion section comprises a shaft extending from the distal end of the body to the grip section of the body, wherein the shaft is formed by the top surface, a first side surface, a second side surface and a bottom surface, further wherein the top surface forms an uppermost surface of the shaft;
wherein the catheter insertion section comprises a catheter locking clamp located at the distal end of the shaft and extending vertically above the shaft; and
wherein the grip section comprises a catheter guide.

2. The catheter placing instrument of claim 1, wherein the grip section further comprises a locking mechanism, wherein the locking mechanism is configured to lock and unlock the catheter locking clamp.

3. The catheter placing instrument of claim 2, wherein the locking mechanism comprises an actuator positioned on the grip section.

4. The catheter placing instrument of claim 1, further comprising measurement markings extending from the distal end of the elongated body along the first side wall and/or the second side wall of the catheter insertion section such that, when the catheter is positioned on the top surface, the measurement markings are viewable.

5. The catheter placing instrument of claim 1, wherein the catheter guide comprises at least two protrusions extending vertically above the top surface.

6. The catheter placing instrument of claim 1, wherein the catheter locking clamp comprises at least two clamp arms configured to lock the catheter in place against the top surface of the elongated body.

7. The catheter placing instrument of claim 1, wherein the catheter insertion section has a height ($H_1$) in a vertical direction that is shorter than a height ($H_2$) of the grip section in the vertical direction.

8. The catheter placing instrument of claim 1, wherein the catheter insertion section has a width ($W_1$) in a transverse direction, and the grip section has a width ($W_2$) in the transverse direction.

9. The catheter placing instrument of claim 8, wherein the width ($W_2$) of the grip section is larger than the width ($W_1$) of the catheter insertion section.

10. The catheter placing instrument of claim 1, wherein the grip section comprises a grip handle.

11. The catheter placing instrument of claim 1, wherein the top surface is flat.

12. The catheter placing instrument of claim 1, wherein the top surface comprises a concave curvature configured to hold the catheter.

13. The catheter placing instrument of claim 1, wherein the catheter placing instrument is configured to place the catheter at a deep anatomical site of a patient.

14. The catheter placing instrument of claim 1, wherein the catheter placing instrument is configured to place an electrical lead having one or more electrical contacts at a deep anatomical site of a patient.

15. A method of surgically placing a tubular medical device at a deep anatomical site of a patient, the method comprising steps of:
  inserting a tubular medical device into an open surgical site;
  providing a placing instrument, the placing instrument comprising:
    an elongated body, the elongated body extending in a longitudinal direction from a proximal end to a distal end, the elongated body having a top surface configured to receive the tubular medical device extending from the proximal end to the distal end, wherein the elongated body comprises a tubular medical device insertion section and a grip section;
    wherein the tubular medical device insertion section comprises a shaft extending from the distal end of the elongated body to the grip section of the body, wherein the shaft is formed by the top surface, a first side surface, a second side surface and a bottom surface, and a locking clamp located at the distal end of the shaft; and
    wherein the grip section comprises a tubular medical device guide;
  placing the tubular medical device on the top surface of the placing instrument such that a distal tip of the tubular medical device is positioned at the distal end of the shaft and the tubular medical device extends through the tubular medical device guide;
  locking the tubular medical device to the placing instrument by clamping the distal tip of the tubular medical device with the locking clamp;
  advancing the distal end of the placing instrument into a deep anatomical site accessed by the open surgical site;
  releasing a release mechanism to unlock the tubular medical device from the placing instrument; and
  removing the placing instrument from the deep anatomical site without moving the tubular medical device.

16. The method of claim 15, wherein the tubular medical device is a catheter.

17. The method of claim 15, wherein the tubular medical device is an electrical lead having at least one electrical contact.

18. The method of claim 15, wherein the placing instrument further comprises measurement markings extending from the distal end of the elongated body along the longitudinal length of the shaft;
  wherein the step of advancing includes advancing the distal end of the tubular medical device to the anatomical site to a desired depth utilizing the measurement markings to determine the depth.

19. The method of claim 15, wherein the step of advancing includes blindly advancing the distal end of the placing instrument into the deep anatomical site by blunt dissection.

20. The method of claim 15, wherein the tubular medical device includes a viewable indicator;
  further wherein the step of removing the placing instrument from the anatomical site without moving the tubular medical device comprises visualizing the viewable indicator to ensure that the tubular medical device is not moved when the placing instrument is removed from the anatomical site.

* * * * *